(12) United States Patent
Maerten et al.

(10) Patent No.: US 7,842,011 B2
(45) Date of Patent: Nov. 30, 2010

(54) MEDICAL INSTRUMENT WITH INJECTION NEEDLES THAT CAN BE SPREAD OUT SIDEWAYS

(75) Inventors: Philippe Maerten, Lausanne (CH); Andreas Efinger, Rietheim (DE); Rainer Hermle, Gosheim (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 12/257,889

(22) Filed: Oct. 24, 2008

(65) Prior Publication Data
US 2009/0112161 A1 Apr. 30, 2009

(30) Foreign Application Priority Data
Oct. 26, 2007 (DE) .................. 10 2007 052 513

(51) Int. Cl.
*A61M 37/00* (2006.01)
(52) U.S. Cl. ...................................... 604/131
(58) Field of Classification Search ............ 604/131, 604/264, 164.01, 106, 107
See application file for complete search history.

(56) References Cited
U.S. PATENT DOCUMENTS
5,419,777 A 5/1995 Hofling 5,538,504 A 7/1996 Linden et al.
6,629,987 B1 * 10/2003 Gambale et al. ............ 606/198
2004/0138621 A1 7/2004 Jahns et al.

FOREIGN PATENT DOCUMENTS
WO 9210142 A1 6/1992
WO 0108741 A1 2/2001

OTHER PUBLICATIONS
European Search Report, EP 08 16 7527; Feb. 19, 2009; 7 pages.
* cited by examiner

*Primary Examiner*—Nicholas D Lucchesi
*Assistant Examiner*—Brooke M Matney
(74) *Attorney, Agent, or Firm*—St. Onge Steward Johnston & Reens LLC

(57) ABSTRACT

A medical instrument comprises a tubular body, housing at least one injection needle with a radially outwardly directed tip portion in an axially undisplaceable manner. A control element serves for deploying the tip of the injection needle out sideways from the tubular body. It is proposed that the control element is housed in the tubular body in an axially displaceable manner, and that said element it in operative connection with the at least one injection needle in such a way that, in a first axially displaced position, the outwardly directed tip portion of the injection needle is fully retracted in the body and, in a second axially displaced position, at least the tip of the outwardly directed tip portion is pressed sideways out from the tubular body (FIG. 5).

18 Claims, 8 Drawing Sheets

MEDICAL INSTRUMENT WITH INJECTION NEEDLES THAT CAN BE SPREAD OUT SIDEWAYS

BACKGROUND OF THE INVENTION

The invention relates to a medical instrument comprising a tubular body housing at least one injection needle.

A medical instrument of this type in the form of a catheter is known from U.S. Pat. No. 5,538,504.

This catheter has a tubular body housing one injection needle with a radially outwardly directed tip portion in an axially undisplaceable manner, and has a control element for deploying the tip of the injection needle out sideways from the tubular body.

A tubular body of the catheter houses inside it an injection needle which has a radially outwardly directed tip portion. In the tubular body there is a corresponding opening, via which at least the tip of the outwardly directed tip portion can pass through radially outwards. Provided in the region of the outwardly directed tip portion is a control element, by means of which the tip portion can be pressed radially outwards as and when required.

Without actuation of the control element, the outwardly directed tip portion is fully retracted in the tubular body. In this state, the catheter can be pushed into a vessel, for example into a urethra.

The control element comprises an inflatable balloon, which is situated in the catheter directly alongside the outwardly directed tip portion. If the balloon is inflated, whether by means of a liquid or a pressurized gas, the inflated balloon presses the tip portion radially outwards, so that at least the tip moves radially outwards beyond the outer side of the tubular body and punctures the vessel. A medicament can then be administered.

After application, the liquid or the pressurized gas is let out again, so that the balloon can contract. The return of the outwardly directed tip portion then takes place on the basis of the elasticity of the outwardly directed tip portion, which usually consists of metallic material.

A disadvantage of this is that it cannot be ensured with absolute certainty that the outwardly directed tip portion will move back again completely into the tubular body.

This is because the tip has punctured the tissue of the vessel and is held relatively firmly there.

This can have fatal consequences when the medical instrument is withdrawn from the vessel, to be specific that the vessel may be damaged, or even lacerated, by the tip still protruding beyond the outer side of the tubular body over the entire length over which it is withdrawn.

From WO 92/10142 it is known to move a number of injection needles out of a tubular body in a circumferentially distributed manner, so that in the case of a relatively large vessel it can be supplied with a medicament at multiple locations circumferentially. Here, the retraction and deployment is controlled by an axial longitudinal displacement of the injection needles. Provided for this purpose in the tubular body is a control element with recessed channels, in which the injection needles can be moved axially back and forth. In the region of the lateral outlets, these channels have outwardly directed curvatures, over which the injection needles then emerge from the tubular body in an outwardly directed manner.

A disadvantage of this structural design is that the injection needles must be axially displaced back and forth in the tubular body, which is problematic in the case of extremely thin injection needles and can lead to them becoming caught or stuck. Considerable design measures have to be taken here to make sure that, before the medical instrument is withdrawn, it is ensured that all the injection needles are fully retracted again.

In the case of the subject matter of the present application, the intended area of use is as an anuscope, i.e. the tubular body is of a considerable length and a considerable diameter and serves the purpose of applying a medicament in a circumferentially distributed manner in the rectum.

If tips of the injection needles were still to protrude radially beyond the tubular body when the instrument is withdrawn from the anus, considerable injuries would occur.

It is therefore an object of the present invention to develop a medical instrument of the above-mentioned type in that the outwardly directed tip portions of the injection needles are moved in a defined manner into the deployed position, and back into the fully retracted position.

SUMMARY OF THE INVENTION

This object is achieved according to the invention by a medical instrument comprising a tubular body, at least one injection needle housed axially undisplaceable in said tubular body, each of said at least one injection needles has a radially outwardly directed tip portion, a control element housed in said tubular body, said control element being axially displaceable within the tubular body, said control element being in a positive operative connection with said at least one injection needle, wherein in a first axially displaced position of said control element said radially outwardly directed tip portion of said needle is fully rejected into said tubular portion and in a second axially displaced portion of said control element at least said tip portion of said needle is positively pushed laterally out from said tubular body by said control element.

These measures have considerable technical advantages in terms of handling. On the one hand, it is possible to house the injection needles in the tubular body in an axially undisplaceable manner. That is to say that these sometimes extremely thin injection needles do not have to be displaced axially, and consequently do not undergo any shearing forces. The control element is designed in such a way that it is axially displaceable and in operative connection with the injection needle in such a way that in one position the curved tip portion is pushed out by the control element, in the other position it is actively fully retracted again in the tubular body by the control element.

This ensures that the outwardly pushed portion is fully retracted again into the tubular body by means of the control element when the latter is axially displaced, so that the risk of injuries when the medical instrument is withdrawn is eliminated completely.

In a further configuration, the control element has a spreading element, which presses the tip portion of the injection needle out sideways beyond the tubular body when the control element is axially displaced.

This measure has the advantage that this spreading element can be used for creating in a defined manner an engaging body that is appropriately designed and suitable for the withdrawing movement.

In a further configuration of the invention, the control element has a retracting element, which fully retracts the tip portion of the injection needle back into the tubular body when the control element is axially displaced from the second position into the first position.

This measure has the advantage of providing a special retracting element which is in operative connection with the injection needle in such a way that it is ensured in an entirely defined manner by this retracting element that the tip portion pressed out sideways is retracted again.

For this purpose, it is proposed in a further configuration that the shaped spreading element is shaped as a spreading wedge, or the retracting element is as a retracting wedge.

This measure has the advantage that the axial, that is to say linear, movement back and forth of the control element can be converted in a mechanically simple way by means of the wedge surface into a radially outwardly directed spreading movement and again into a radially inwardly directed retracting movement on the injection needle. By providing wedges with wedge surfaces, a mechanically fixed connection between the control element and the respective injection needle is not necessary, but instead it is sufficient if the wedge surfaces slide past corresponding locations on the injection needle in order to control the movement.

This also makes it possible for these two parts to be easily separated from one another and cleaned after use. The configuration, and in particular the slope, of the wedges or the wedge surface allows different pushing-out or retracting lengths to be accomplished.

In a further configuration of the invention, the control element must be moved out of the first and second axially displaced positions initially into a twisted position by means of a turning movement before it is moved into the other respective axially displaced position.

This measure has the advantage that the control parts on the control element can be made very compact and do not hinder one another. This means that the spreading element or the spreading wedge does not lie in the direct path of displacement of the retracting element or the retracting wedge, that is to say do not hinder one another.

In a further configuration, it is provided that the wedge surfaces of the wedge part and the retracting part are circumferentially offset.

This measure has the advantage that these two wedges can be spaced apart axially very close together and consequently the device is very compact. In the one turned position, only one wedge is in operative connection with the injection needle, in the other turned position it is then correspondingly only the other wedge.

In a further configuration of the invention, there is a positive control, which controls the movement of the control element in such a way that there is a closed rectangular control path.

This measure has the advantage that the control movement is predetermined for the physician. To deploy the tip of the injection needle, he carries out for example an axial, and distally directed, advancing movement, it being possible for this also to be clearly defined by corresponding final locking points. The following turning movement has the effect that the spreading wedge is disengaged from the injection needle and the retracting wedge is turned into a position in which it can enter into operative connection with the injection needle. A subsequent, proximally directed displacement movement, again extending axially, has the effect that the retracting wedge comes into operative connection with the injection needle and retracts it. As already mentioned, the retracting wedge and the spreading wedge then do not disturb one another as a result of the circumferential offset of the wedge surfaces. Before a renewed pushing-out movement is carried out, the spreading element is again circumferentially turned in the opposite sense, so that the spreading element is again at its starting point and available for a further pushing-out operation.

In a further configuration of the invention, the tubular body houses multiple injection needles and the multiple injection needles can be controlled by a single control element.

This measure has the advantage that only a single control element has to be provided and that the multiple injection needles can be simultaneously pushed out sideways or retracted again.

In a further configuration of the invention, for this purpose the control element has notches, in which at least the outwardly directed tip portion of the injection needles can be received.

This measure has the advantage that, seen overall, the device is less voluminous, since the curved tip portions of the cannulas are housed in the notches in the control element.

In a further configuration of the invention, the outwardly directed tip portions of the injection needles have a first portion, which can enter into operative connection with the spreading element, and a second portion, which can enter into operative connection with the retracting element.

This measure has the advantage that the operative connection between the control element and the curved portion of the injection needle can be established at separate locations in a simple way in terms of structural design.

In a further configuration of the invention, the second portion of the injection needles is formed as a wedge, which is in connection with the retracting wedge when the injection needles are retracted.

This measure has the advantage that provision of this additional wedge ensures that, as a result of the two wedge surfaces of this wedge and of the retracting wedge sliding past one another, the outwardly bent tip portions can be retracted in an entirely defined manner and brought into a defined end position in which it is absolutely ensured that even the tips no longer protrude sideways beyond the tubular body. This is also ensured if contamination such as body fluids, blood or the like should happen to get into the interior of the tubular body via the outer openings. Even contamination adhering to the wedge surfaces would be pushed to the side by the wedge surfaces sliding past one another, so that the control works satisfactorily even in a highly contaminated state.

In a further configuration of the invention, the multiple injection needles are fitted in a protective tube.

As already mentioned, a mechanically permanent fixed connection between the control element and the injection needles is not necessary, since the radial movement of the injection needles is controlled by means of the spreading elements or wedges. It is therefore adequate if, after assembly, the control element and the injection needle are arranged in a predefined position in relation to one another, without having to be mechanically connected to one another in the control region. This is then additionally improved by multiple injection needles, if provided, being fitted in a protective tube. In this way, the injection needles can be aligned in an exactly position-defined manner already during production. This also makes assembly and disassembly easier, since the sometimes extremely thin and long injection needles are protected by the protective shaft.

In a further configuration of the invention, the control element can be inserted into the tubular body from the proximal end.

This measure has the advantage that, after assembly, for example of the protective shaft in the tubular body, this control element can be inserted in proximally and positioned exactly in the desired position alongside the injection needles. This inserting in of the control element can be monitored very well during assembly. During disassembly, the control element can also be easily withdrawn again, without the risk of thereby damaging an injection needle.

In a further configuration of the invention, the control element is shaped as a rod-shaped body, which distally bears the spreading element and the retracting element.

In particular in the case of the configuration with multiple injection needles and with the notched body, this has the advantage that the rod-shaped body can be inserted into the tubular body from the proximal end in such a way that the multiple injection needles can enter the notches in an exactly aligned manner. This facilitates handling, in particular, during assembly and disassembly.

In a further configuration of the invention, the rod-shaped body has a control grip, which is proximally angled away from the rod-shaped body.

This measure has the advantage that the control or the movement of the control element can be carried out by means of the control grip. The handling person can grasp the control grip and bring the control element into the different displaced positions or turned positions, this being further facilitated considerably by the positive control.

In a further configuration of the invention, the rod-shaped body can be pushed into the protective shaft centrally between the multiple injection needles from the proximal end.

As previously mentioned, this measure has the particular advantage in the assembly and disassembly of multiple injection needles. In assembly, the protective shaft with the multiple injection needles can first be pushed into the tubular body and positioned. Subsequently, the rod-shaped body is then brought between the injection needles from the proximal end in an exactly positioned manner.

In a further configuration of the invention, the medical instrument is formed as an anuscope.

This measure has the advantage that the invention is particularly suitable for this area of use in particular, since corresponding injection treatments can also be carried out if appropriate at multiple locations spaced apart from one another, it being ensured that no protruding injection needle tips can cause injuries during withdrawal or axial displacement.

It goes without saying that the features mentioned above and those still to be explained below can be used not only in the combination respectively specified but also in other combinations or on their own without departing from the scope of the present invention.

BRIEF DESCRIPTION OF THE DRAWINGS

The invention is described in more detail and explained below on the basis of a selected exemplary embodiment in conjunction with the accompanying drawings, in which.

DETAILED DESCRIPTION OF A PREFERRED EMBODIMENT

Figure 1:
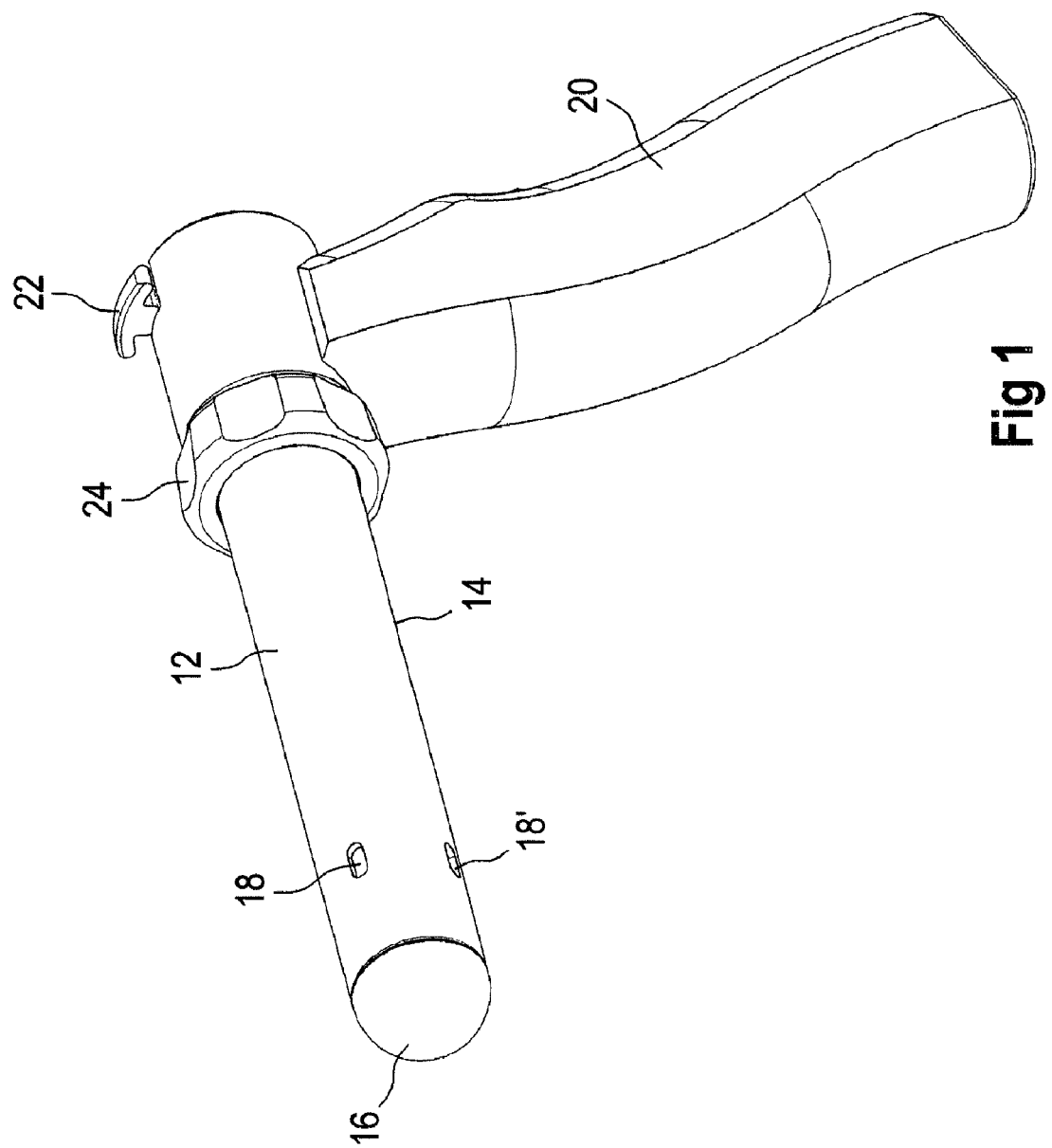
FIG. 1 shows a perspective view of a component of the medical device, to be specific the tubular body, from which the handle laterally projects.

A medical instrument represented in the figures is designated as a whole by the reference numeral 10. This medical instrument is an anuscope.

It can be seen from FIG. 1 that the medical instrument has an elongated tubular body 12 in the form of a tube 14, which is terminated at the distal end by means of a half-round cap 16. The length and diameter of the tube 14 are formed such that it can be pushed into the anus of a human body.

In the region of the end cap 16, four openings 18, 18' are provided in the tubular body 12 in a circumferentially distributed manner, the purpose of which will be explained later.

At the proximal end, the tubular body 12 is connected to a grip 20, which projects laterally at an angle and by means of which the handling person can grasp the medical instrument 10 with one hand. A union nut 24 provides a releasable connection between the grip 20 and the tube 14. A detent 22 is provided for the purpose of locking further components, still to be described below, which are pushed into the tube 14 from the proximal end.

Figure 2:
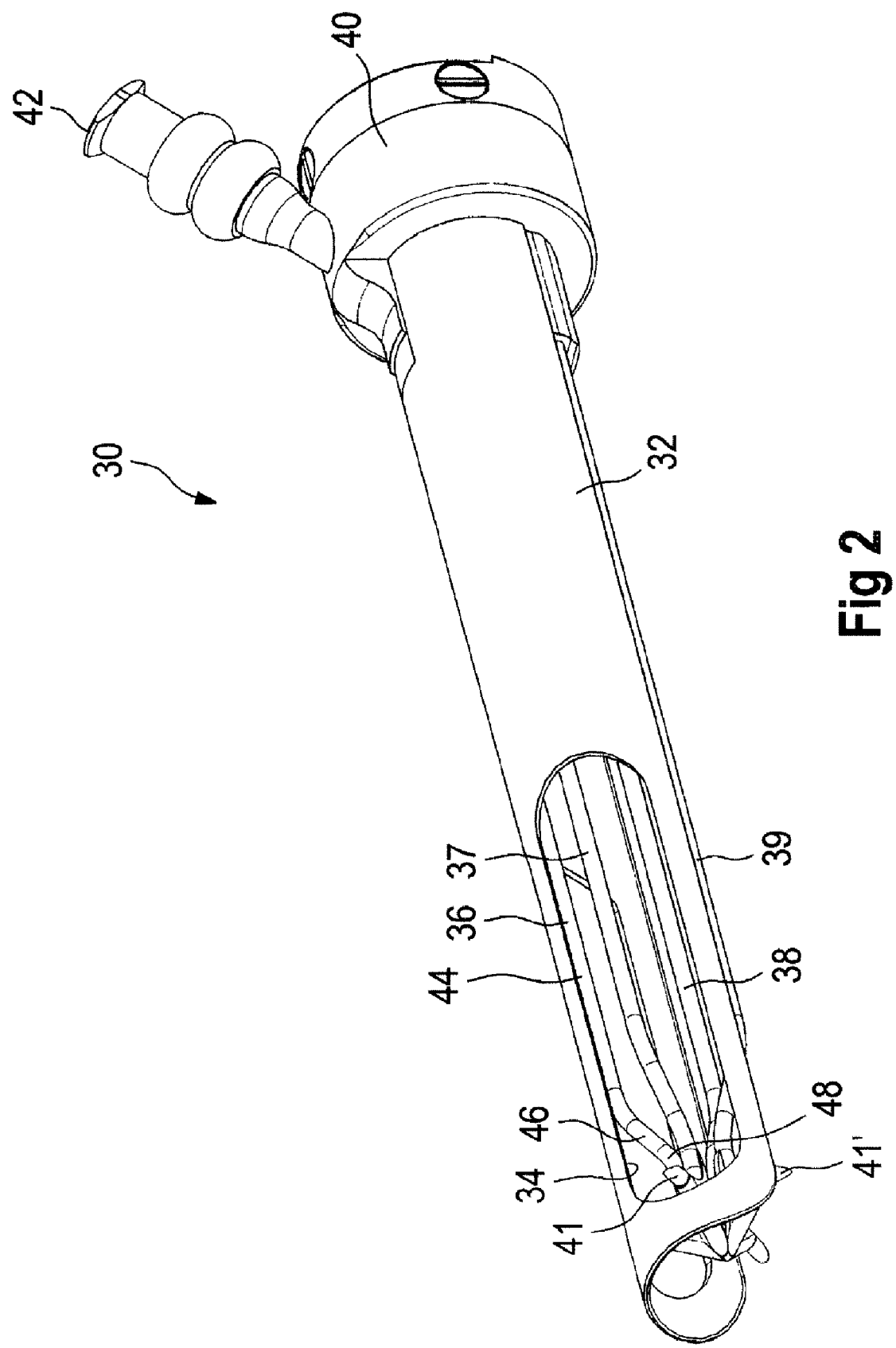
FIG. 2 shows a perspective view of a further component, to be specific a protective shaft, in which four injection needles are housed.

One of these further components is the protective shaft 30 represented in FIG. 2.

The protective shaft 30 likewise has a tube 32, the outside diameter and length of which are dimensioned such that it can be inserted into the tube 14 of the tubular body 12 in a fitting manner.

The tube 32 has multiple windows 34, by means of which a view into the anus or into a body cavity is afforded from the proximal end.

Four injection needles 36, 37, 38, 39 are fitted in a circumferentially evenly distributed manner in the inner space of the tube 32. All four injection needles 36 to 39 are proximally fastened to a flange 40, which is provided with a LUER connection 42. By means of the LUER connection 42 and the flange 40, all four injection needles 36, 37, 38, 39 can be provided with a liquid, which respectively emerges at a tip 41, 41'. For the sake of an overview, only the two tips 41, 41' of the four injection needles 36 to 39 are designated.

Each of the injection needles 36 to 39 has an elongated cannula 44, which goes over via a radially inwardly directed curvature 46 into a radially outwardly directed tip portion 48, 48', which then ends in the corresponding tip 41, 41'. The more specific configuration and purpose are described and explained in more detail later on the basis of FIGS. 9 to 12.

Figure 3:
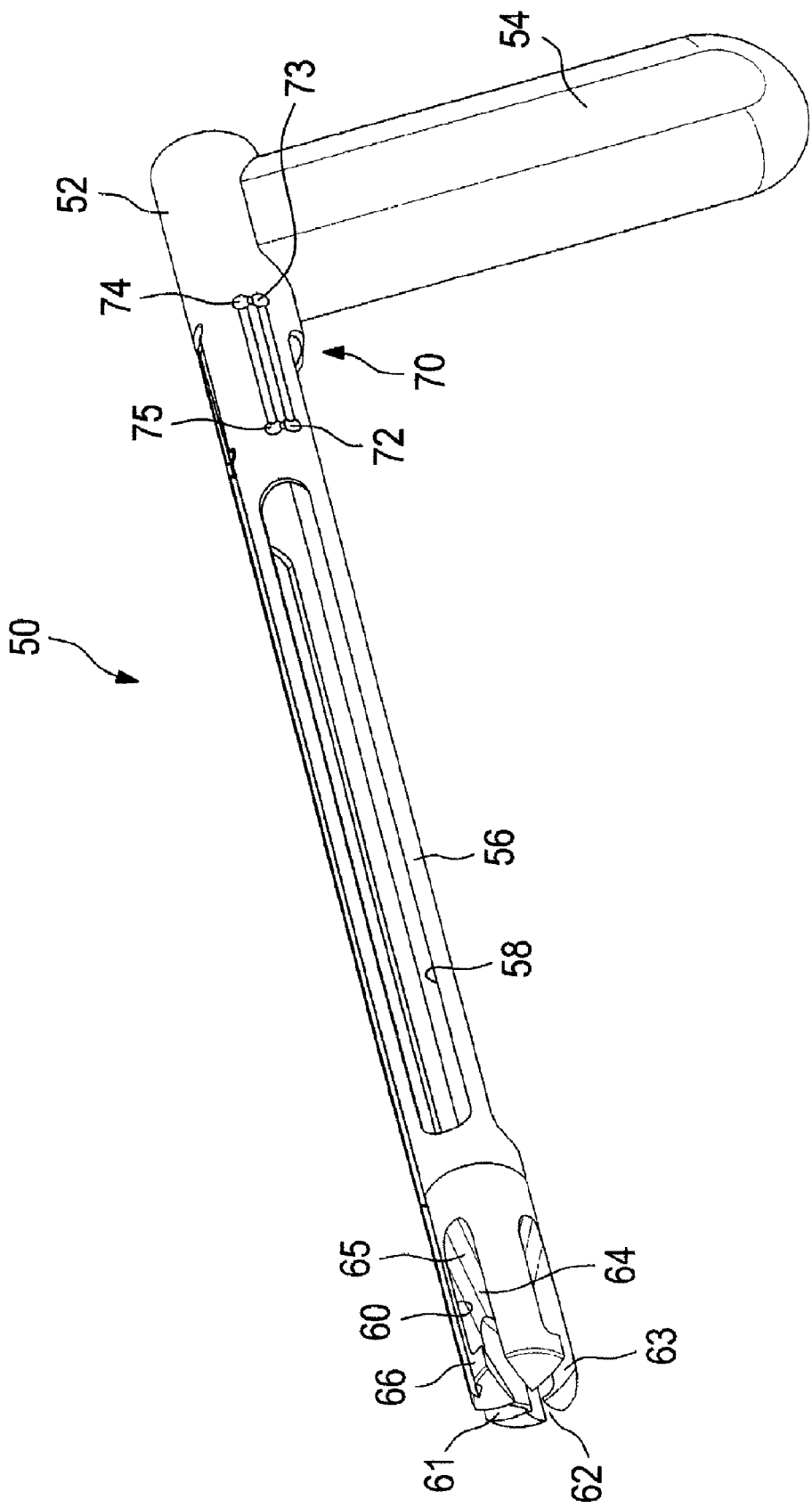
FIG. 3 shows a corresponding perspective representation of a further component of the medical device according to the invention, to be specific the control element with the control grip at the proximal end.

In FIG. 3, a further component of the medical instrument 10 can be seen, to be specific the control element 50.

The control element 50 has a body in the form of an elongated rod 52, which proximally has a control grip 54, laterally projecting in the exemplary embodiment represented. The rod 52 is formed over most of its longitudinal extent as a hollow body 56 and has multiple windows or clearances 58. At the distal end, the body has four circumferentially distributed notches 60, 61, 62, 63, which are configured in their width, length and depth such that the curved tip portion of their respective injection needle can be housed therein.

Formed at the proximal end of each notch 60, 61, 62, 63 is a spreading wedge 64, which has a wedge surface 65 which, seen from proximal to distal, slopes radially inwards. Lying opposite the spreading wedge 64 is a corresponding retracting wedge 66, which has a corresponding wedge surface 67. The configuration and purpose of the wedges are described in more detail in conjunction with FIGS. 9 to 12.

It should be mentioned that the wedge surface 65 of the spreading wedge 64 is circumferentially offset somewhat with respect to the wedge surface 67 of the retracting wedge 66.

Cut into the outer side of the hollow body 56 alongside the control grip 54 is a control cam 70, which is rectangular. This control cam 70 has a first locking point 72, a second locking point 73, spaced apart proximally from the first, a third locking point 74, offset circumferentially with respect to the second, and a fourth locking point 75, situated distally with respect to the third and correspondingly offset circumferentially with respect to the first locking point 72. On the inner side of the protective shaft 30, in the region of the flange 40, there projects a corresponding spring-loaded pin-shaped locking element, which engages in the control cam 70.

In the assembly of the medical instrument 10, first the protective shaft from FIG. 2 is inserted into the tube body 12 from the proximal end and locked in the appropriate position by means of the detent 22. As this happens, the four tips 41, 41' of the injection needles 36 to 39 come to lie in the region of the openings 18, 18'. Subsequently, the control element 50 that can be seen from FIG. 3 is inserted into the protective shaft 30, already fitted in the tubular body 12, from the proximal end.

In this case, the control element 50 is inserted in such that it moves itself centrally into the enclosure made up of the four circumferentially distributed injection needles 36 to 39, to be precise in such a way that the curved tip portions 48, 48' and the curvature 46 come to lie in the notches 60 to 63. The alignment is then such that the control element 50 locks with the previously described detent in the first locking point 72.

Figure 4:
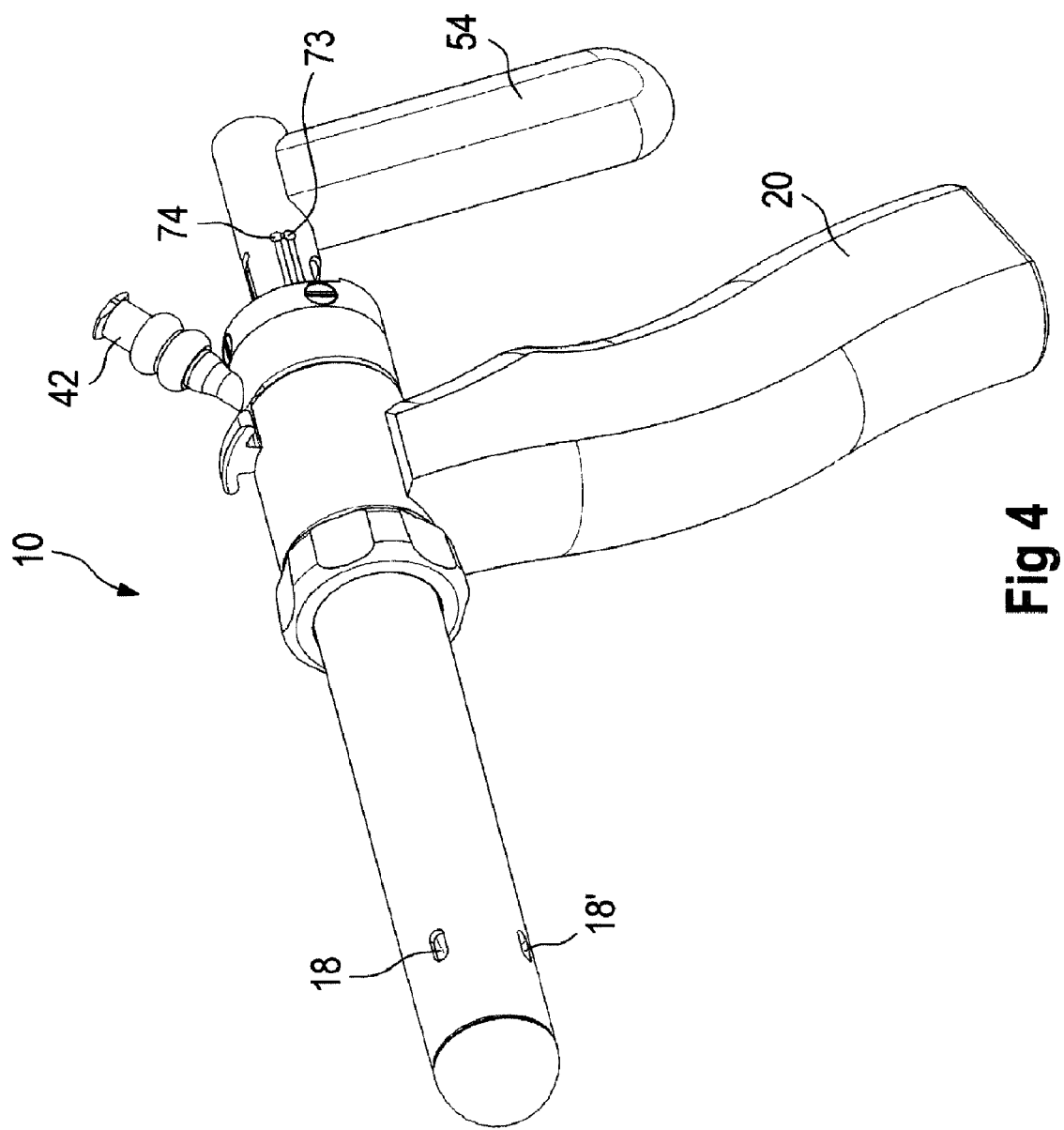
FIG. 4 shows the medical instrument in the assembled state, the protective shaft from FIG. 2 first having been inserted into the tubular body from the proximal end and subsequently the control element that can be seen from FIG. 3 having been inserted into the protective shaft from the proximal end to a first position.

This final assembly position is represented in FIG. 4.

Figure 5:
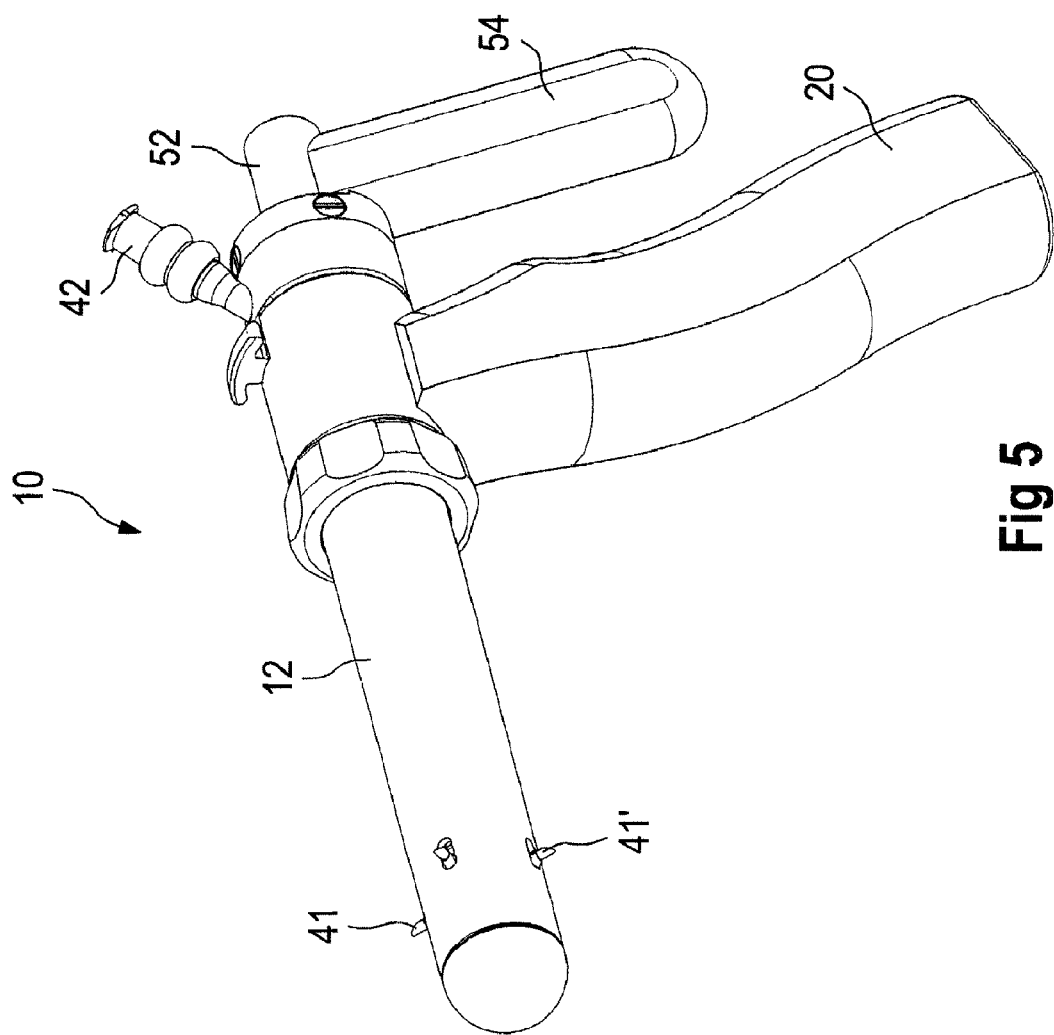
FIG. 5 shows a second displaced position, in which the control element has been axially displaced in the distal direction and, as a result, the tips have been pushed out sideways beyond the tubular body.

For the spreading out sideways, the control element 50 is displaced from proximal to distal to such an extent that the detent engages at the locking point 73. The situation is represented in FIG. 5. In this case, the wedge surfaces 65 of the spreading wedges 64 have respectively come into contact with the curvature 46 of an injection needle 36 to 39 and have pressed it radially outwards, to be precise to such an extent that the tips 41, 41' of said needles reach radially beyond the outer side or outer surface of the tube body 12. A medicament can then be applied by means of the injection needle via the LUER connection 42 at four circumferentially offset locations, for example in the rectum if the medical instrument is formed as an anuscope.

In the exemplary embodiment represented, only the tips of the injection needles have being moved out sideways. It is obvious that the injection needles can be moved out over a longer portion if it is desired that the injection needles penetrate relatively deep into the tissue or into the muscles. The diameter and length of injection needles may vary, so that different groups of needles can be used, depending on the patient or type of treatment to be carried out. One possible treatment is that for incontinence, in which case a substance is injected by means of the injection needles into the sphincter.

Before withdrawal of the control element 50, it is twisted about a longitudinal axis by means of the control grip 54, whereby the detent is moved from the second locking point 73 into the third locking point 74.

Figure 6:
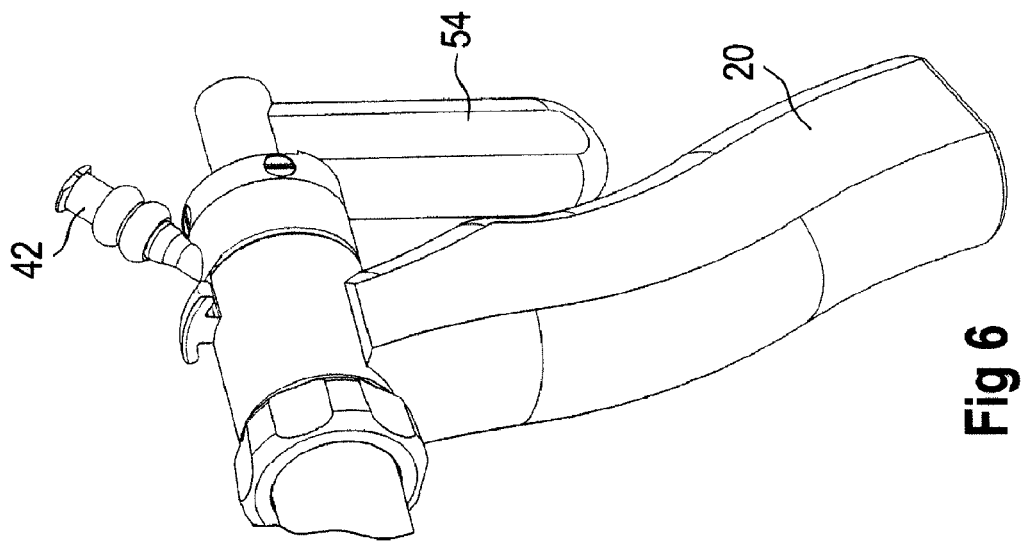
FIG. 6 shows a turned position of the control element before latter is axially withdrawn again.

This position is represented in FIG. 6. From this position, the control element 50 can then be withdrawn again proximally, after which it then reaches the fourth locking point 75. In this position, the control grip 50 is then displaced circumferentially in the opposite direction, so that the initial locking position 72 is again reached, this corresponding to the position of FIG. 4.

When the control element 50 is moved proximally, the tip portions 48, 48' of the injection needles 36 to 39 are drawn radially in again, to be precise to such an extent that the tips 41, 41' no longer reach out beyond the outer side of the tube body 12, that is to say the situation of FIG. 4 is reinstated.

This sequence of movements and control is now to be explained in more detail on the basis of the sectional representations of FIG. 7 to FIG. 12.

Figure 7:
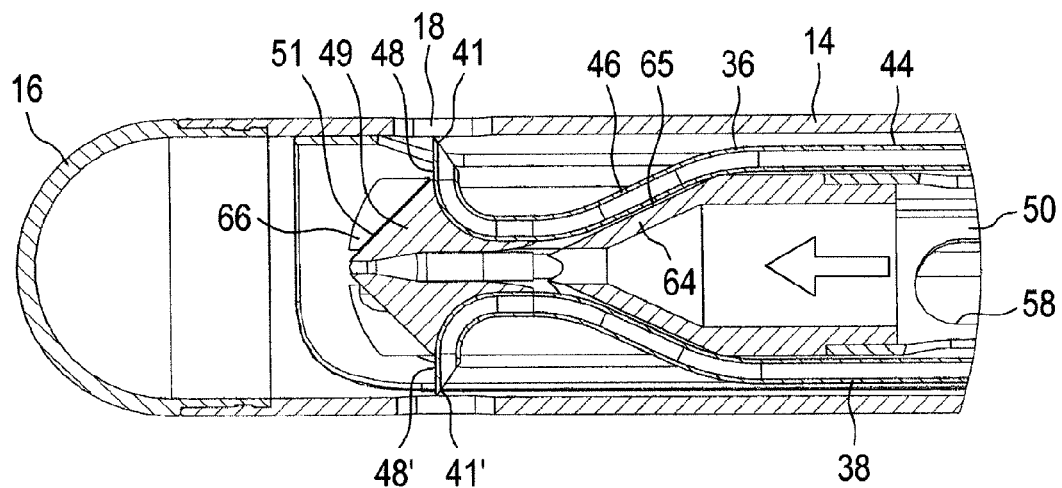
FIG. 7 shows a longitudinal section in the region of the distal end of the medical device in a position such as that represented in FIG. 4.

FIG. 7 represents a longitudinal section in the distal end region of FIG. 5, the section being taken such that two diametrically opposite injection needles 36 and 38 are shown in section. It can be seen that the injection needle 36 has a portion extending in a straight line in the form of a cannula 44, which goes over via a radially inwardly directed curvature 46 into the radially outwardly curved tip portion 48, which opens out in the tip 41. Additionally fitted in the region of the tip portion 48, seen distally from the latter, is a wedge 49, the wedge surface 51 of which is aligned such that it can come into contact with the corresponding wedge surface 67 of the retracting wedge 66, as still to be explained later.

Inserted in centrally between the injection needles 36 and 38 is the control element 50, to be precise in such a way that its spreading wedge 46 or its wedge surface 65 has come to lie against the inwardly directed curvature 46.

As previously mentioned, the wedge surface 65 of the spreading wedge 64 and the wedge surface 67 of the retracting wedge 66 are circumferentially offset in relation to one another, to be precise by the circumferential extent of the transition from the second locking point 73 to the third locking point 74 or the transition from the fourth locking point 75 to the first locking point 72 (see FIG. 3).

It can therefore be seen in FIG. 7 that, here in this position, the retracting wedge 66 or its wedge surface is not in engagement with the wedge surface 51 of the wedge 49. If the control element 50 is then displaced in the distal direction, as indicated in FIG. 7 by an arrow, the curved tip portions 48, 48' are pressed radially outwards, so that their tips 41, 41' emerge via the outer side of the tubular body or the tube 14, as is represented in FIG. 8.

Figure 8:
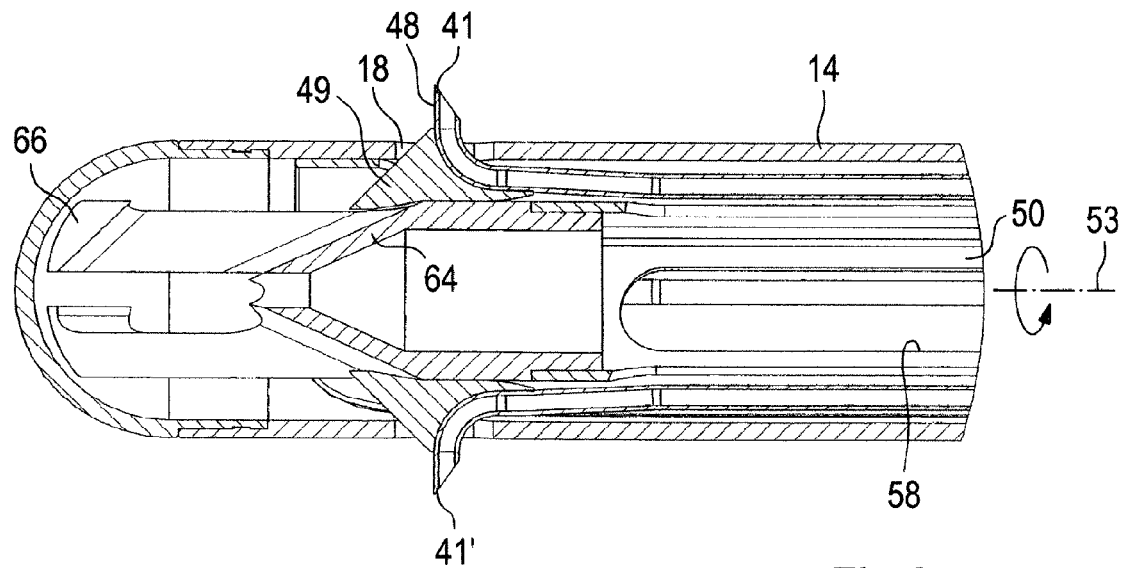
FIG. 8 shows the corresponding longitudinal section that corresponds to the situation of FIG. 5.

The transition from FIG. 7 to FIG. 8 consequently corresponds to the transition from FIG. 4 to FIG. 5.

The locking element, not represented here, has then moved in the control cam 70 from the first locking point 72 to the second locking point 73. A further advancement of the control element 50 is not possible.

In preparation for the retracting movement, the control element 50 is first turned about it is central longitudinal axis 53, as represented in FIG. 8 by an arrow.

Figure 9:
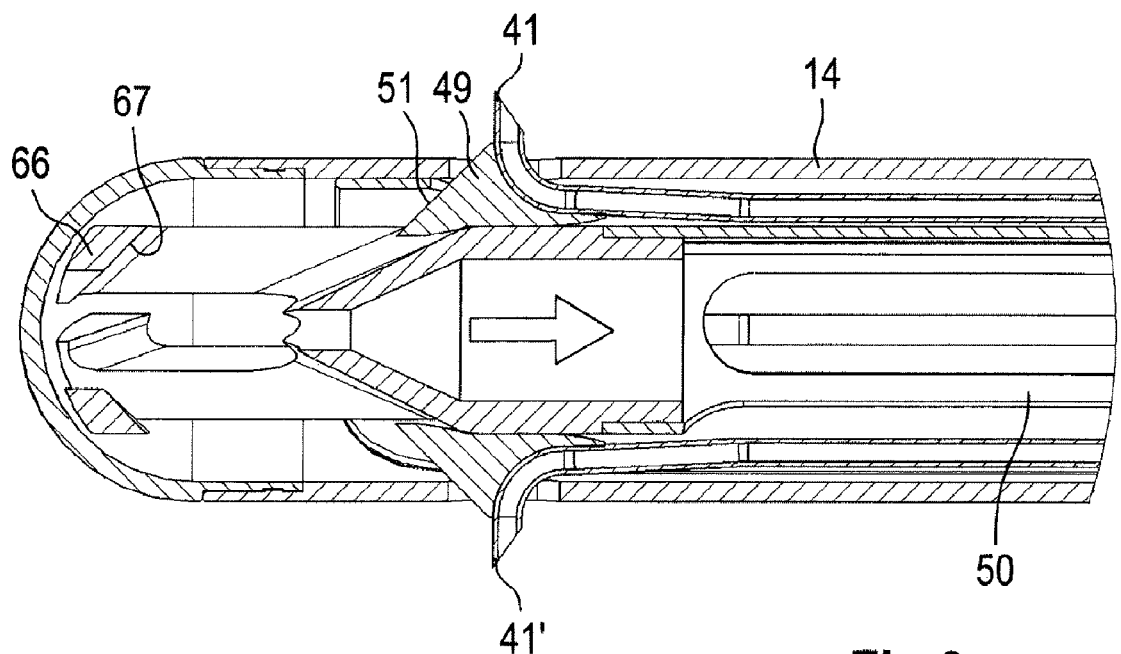
FIG. 9 shows a corresponding longitudinal section that corresponds to the situation of FIG. 6.

The turning movement, seen from proximal to distal, takes place anticlockwise, to be precise until the detent has locked in the fourth locking point 74. This turning movement corresponds to the transition from FIG. 5 to FIG. 6 or the transition from FIG. 8 to FIG. 9. In FIG. 9 it can then be seen that the wedge surface 67 of the retracting wedge 66 is now in alignment with the wedge surface 51 of the wedge 49.

Figure 10:
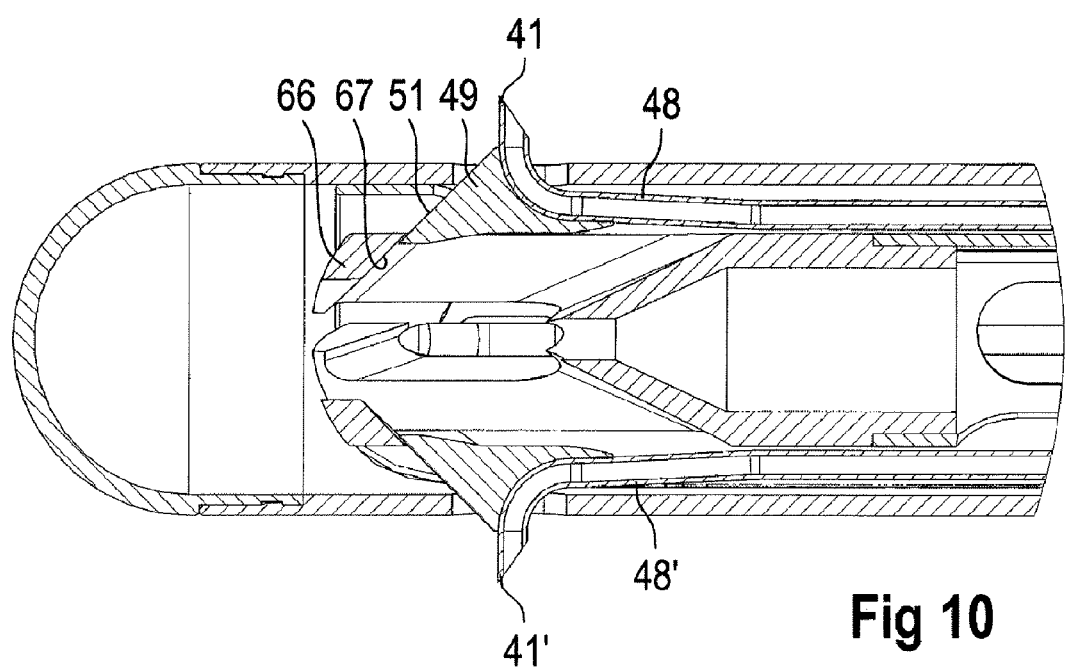
FIG. 10 shows a representation comparable to FIG. 9, the control element having being drawn back to such an extent that its retracting part is just coming into engagement with the wedge on the curved tip portion of injection needle.

If the control element is then drawn from distal to proximal, which takes place by means of the control grip 54, the wedge surface 67 of the retracting wedge 66 approaches the previously mentioned wedge surface 51 of the wedge 49, as is represented in FIG. 10, and comes into engagement with it. On further movement in the proximal direction, the wedge surface 67 of the retracting wedge 66 causes a radially inwardly directed retraction of the tip portions 48 or 48' of the injection needles, the end state being represented in FIG. 11.

Figure 11:
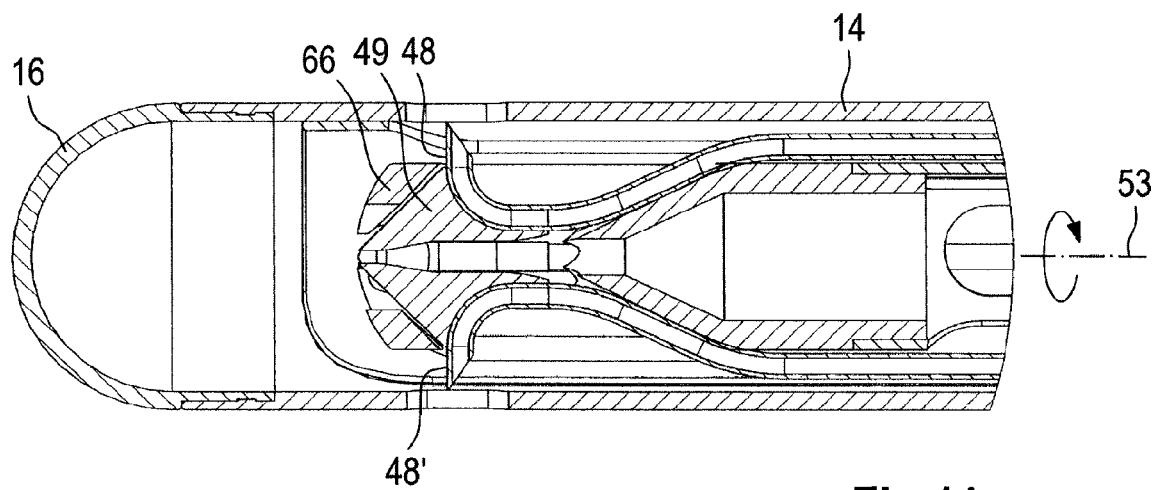
FIG. 11 shows a representation corresponding to FIG. 10 with the control element fully withdrawn and, as a result, a fully retracted tip portion of an injection needle.

It can be seen from the sectional representation of FIG. 11 that the tip portions 48, 48' are fully retracted again in the interior of the tubular body 12. This is positively controlled and ensured. In the position of FIG. 6 or 11, the locking element is locked in the fourth locking point 75 of the positive control 70. It can be seen from FIG. 11 that, in this turned position of the control element 50, the wedge surface 67 of the retracting wedge 66 would hinder renewed spreading. As a result, the control element 50 is twisted again about its longitudinal axis 53, to be precise, seen from proximal to distal, now clockwise, whereby the transition from the fourth locking point 75 to the first locking point 72 is achieved.

Figure 12:
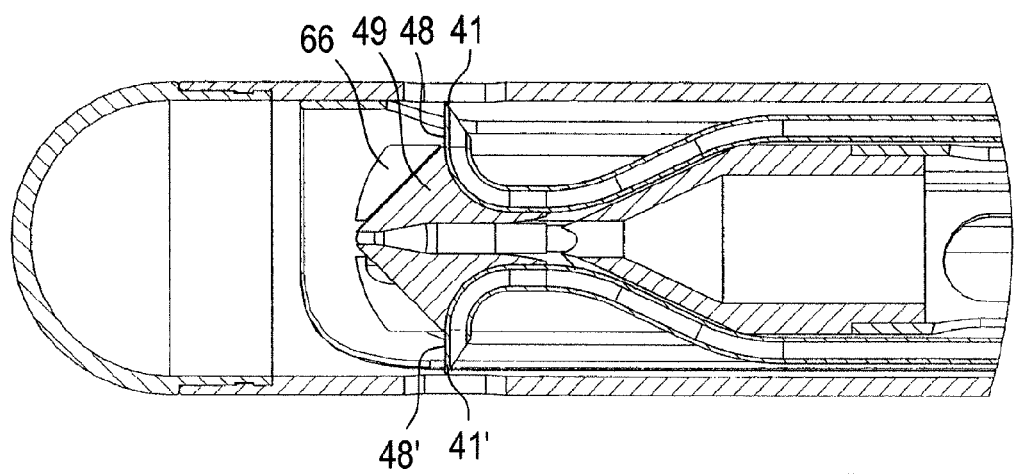
FIG. 12 shows the starting situation again, after twisting of the control element about the longitudinal axis, this starting situation corresponding again to the situation of FIG. 7 or FIG. 4.

This situation is represented in FIG. 12, the situation of FIG. 12 being the same situation as that of FIG. 7. Consequently, the device would therefore be ready to carry out a renewed cycle of movements.

Depending on the configuration of the device, the parts represented in FIGS. 2 and 3 may be formed as multi-use parts or single-use parts. As a result, there is no need for cleaning and disinfection of the cannulas, which would be laborious in the case of very long and thin cannulas. It is also possible to form, for example, just the component represented in FIG. 2 as a disposable part.

To facilitate the assembly and positioning, it may also be envisaged to produce the tubular body 12 from a transparent material and, if appropriate, provide additional illumination or form the rod-shaped body from FIG. 3 as an illuminated rod, so that it can be connected to a light source that is not represented here.

What is claimed is:

1. A medical instrument, comprising
    a tubular body,
    at least one injection needle housed in said tubular body and longitudinally undisplaceable in view of said tubular body,
    each of said at least one injection needle has a radially outwardly directed tip portion,
    a control element housed in said tubular body, said control element being axially displaceable within said tubular body,
    said control element being in a positive operative connection with said at least one injection needle, wherein
    in a first axially displaced position of said control element said radially outwardly directed tip portion of said needle being positively fully retracted into said tubular portion by said control element, and
    in a second axially displaced position of said control element at least said tip portion of said needle being positively pushed laterally out from said tubular body by said control element,
    wherein said control element has a retracting element which fully retracts said tip portion of said at least one injection needle back into said tubular body when said control element is axially displaced from said second position into said first position.

2. The medical instrument of claim 1, wherein said control element has a spreading element which pushes said tip portion of said at least one injection needle sideward out beyond said tubular body when said control element is axially displaced from the first position to said second position.

3. The medical instrument of claim 2, wherein said spreading element is shaped as a spreading wedge.

4. The medical instrument of claim 1, wherein said retracting element is shaped as a retracting wedge.

5. The medical instrument of claim 1, wherein said control element is moved out of said first and said second axially displaced positions into a twisted position by means of a turning movement before said control element is moved into said other respective axially displaced position.

6. The medical instrument of claim 5, wherein a control having a closed, rectangular control path is provided, said control controlling said movement of said control element between said different positions in said control path.

7. The medical instrument of claim 6, wherein said control element has a spreading element which is formed as a spreading wedge and wherein said control has a retracting element which is designed as a retracting wedge wherein a wedge surface of said spreading wedge and a wedge surface of said retracting wedge are circumferentially offset in relation to one another.

8. The medical instrument of claim 1, wherein said tubular body houses multiple injection needles and wherein said multiple injection needles can be controlled by a single control element.

9. The medical instrument of claim 8, wherein said single control element has notches, in which notches at least said outwardly directed tip portion of said multiple injection needles can be received.

10. The medical instrument of claim 8, wherein said multiple injection needles are fitted in a protective shaft.

11. The medical instrument of claim 10, wherein said protective shaft can be inserted into said tubular body from a proximal end thereof.

12. The medical instrument of claim 1, wherein said control element has a spreading element and a retracting element, and wherein said outwardly directed tip portions of said injection needles have a first portion which can enter into operative connection with said spreading element, and a second portion which can enter into operative cooperation with said retracting element.

13. The medical instrument of claim 12, wherein said second portion is shaped as a wedge which is in operative connection with said retracting element when said injection needle is retracted.

14. The medical instrument of claim 1, wherein said control element can be inserted from a proximal end of said tubular body.

15. The medical instrument of claim 1, wherein said control element is shaped as a rod-shaped body bearing a spreading element and a retracting element.

16. The medical instrument of claim 15, wherein said control element has a control grip which is proximally angled away from said rod-shaped body.

17. The medical instrument of claim 1, wherein multiple injection needles are present which are fitted in a protective shaft, and wherein said control element has a rod-shaped body which can be inserted into said protective shaft between said multiple injection needles from a proximal end.

18. The medical instrument of claim 1, wherein it is an anuscope.

* * * * *